Oct. 26, 1965 C. LEIDY Plant Pat. 2,565
HYBRID TEA ROSE PLANT
Filed March 2, 1964
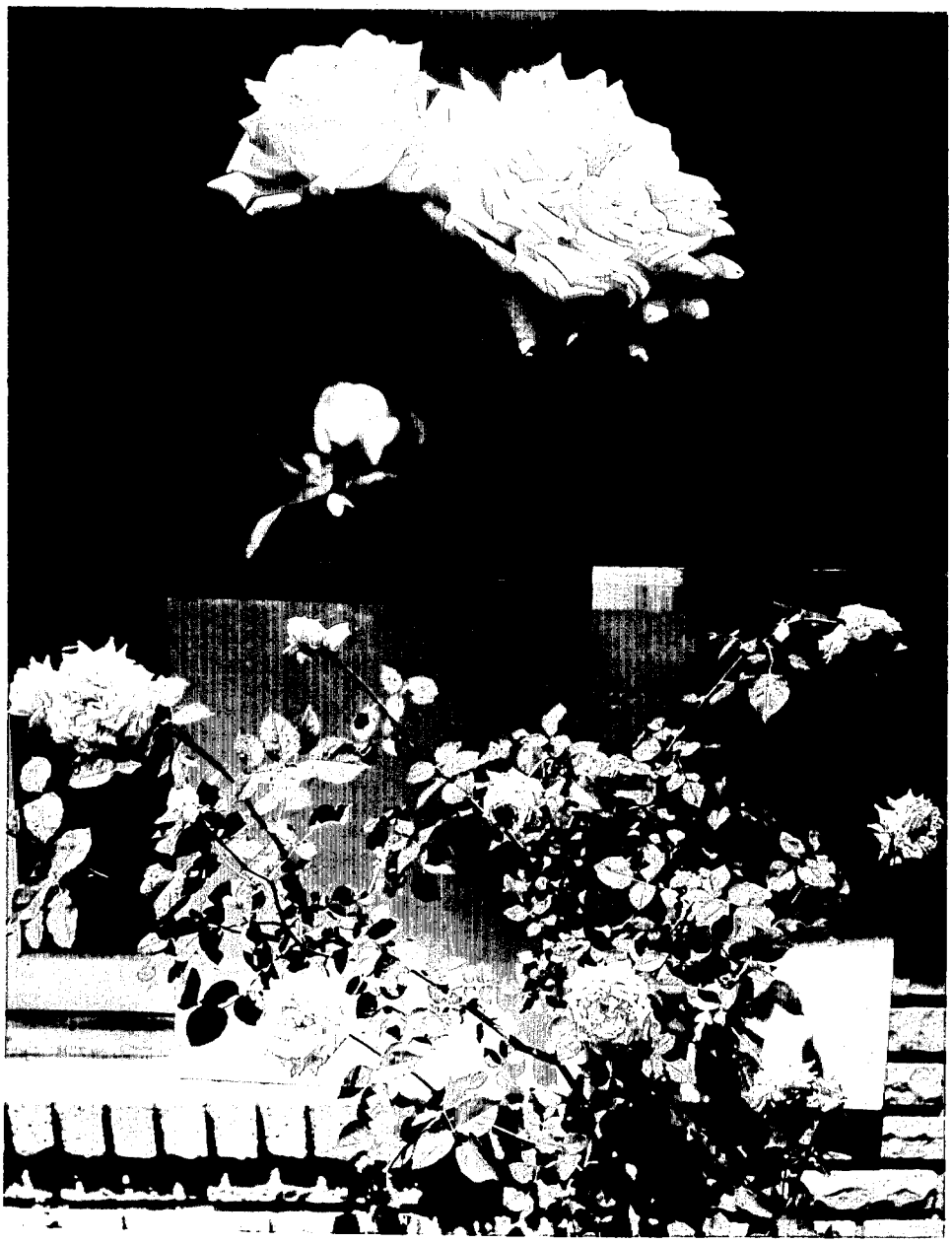

United States Patent Office

Plant Pat. 2,565
Patented Oct. 26, 1965

2,565
HYBRID TEA ROSE PLANT

Charles Leidy, 4506 Shoal Creek Blvd., Austin 5, Tex.

Filed Mar. 2, 1964, Ser. No. 348,889
1 Claim. (Cl. (Plt.—18)

The present invention relates to a new and distinct variety of rose plant of the hybrid tea class. The new rose originated as a whole bud sport of the variety "Tip Toes" (Plant Patent No. 849). The rose of the present invention is readily distinguished from the "Tip Toes" rose primarily by the differencies in color and petalage. The new variety was discovered by me on a "Tip Toes" bush which I had purchase and planted on my own property at 4506 Shoal Creek Boulevard, Austin 5, Texas.

The new variety may be distinguished from its parent in a number of ways. First, the number and color of the petals are entirely different although the size of the blossoms are substantially the same. In the new rose, the bloom is light pink at the bottom of the petals with a shading to a darker pink at the top on both sides of the petals as contrasted with the parent in which the petals are Rose Red to Spectrum Red with an overlay of Lemon Yellow, which slowly changes to Deep Rose Pink. When the bud first begins to open, it is yellow to creamy pink at the base of the petals both on the inside and outside thereof. Secondly, the petals are slightly serrated on the top edge and each bloom of the new rose will contain approximately 100 petals as contrasted with the parent in which the petals number about 25. Thirdly, the bush of the new rose is almost thornless in comparison with the parent.

Referring to Wilson's Horticultural Color Chart No. 2, the deepest pink of petals is one of Porcelain Rose, Plate 620/1, page 147, shaded to a lighter pink which appears to correspond most closely to Orient Pink, Plate 416/3, page 124.

I have propagated this rose by cutting the sport branch off of the parent plant, rooting it and then taking cuttings therefrom and propagating the rose from the cuttings at my home at 4506 Shoal Creek Boulevard, Austin 5, Texas. All cuttings came true to the color of the sport.

The accompanying drawing shows a specimen plant of the new variety in its natural colors, at least as near as is possible to reproduce the natural colors by photographic processes.

I claim:

A new and distinct variety of rose plant of the hybrid tea class characterized by the differences in color of the petals from those of the parent ("Tip Toes" No. 849), by the larger number of petals in each bloom, by the serrations on the top edges of the petals and by the bush which is almost thornless.

No references cited.

ABRAHAM G. STONE, *Primary Examiner.*